United States Patent [19]
Mount et al.

[11] Patent Number: 5,455,423
[45] Date of Patent: Oct. 3, 1995

[54] GAS BUBBLE DETECTOR

[75] Inventors: Bruce E. Mount, Diamond Bar; David E. Burchfield, Rancho Cucamonga; John M. Hagey, Alta Loma, all of Calif.

[73] Assignee: Orbital Sciences Corporation, Dulles, Va.

[21] Appl. No.: 112,008

[22] Filed: Aug. 25, 1993

[51] Int. Cl.$^6$ .................................................. G01N 21/01
[52] U.S. Cl. ............................................ 250/343; 356/440
[58] Field of Search ................................. 250/343, 576; 356/440

[56] References Cited

U.S. PATENT DOCUMENTS

| | | | |
|---|---|---|---|
| 3,705,771 | 12/1972 | Friedman et al. | 250/576 |
| 3,898,637 | 8/1975 | Wolstenholme | 128/DIG. 13 |
| 4,344,429 | 8/1982 | Gupton et al. | 250/574 |
| 4,371,786 | 2/1983 | Kramer | 250/343 |
| 5,078,683 | 1/1992 | Sancoff et al. | 604/67 |

*Primary Examiner*—Carolyn E. Fields
*Attorney, Agent, or Firm*—Jenner & Block

[57] ABSTRACT

A gas bubble detector having a modulated IR source focused through a bandpass filter onto a venturi, formed in a sample tube, to illuminate the venturi with modulated filtered IR to detect the presence of gas bubbles as small as 0.01 cm or about 0.004" in diameter in liquid flowing through the venturi. Means are provided to determine the size of any detected bubble and to provide an alarm in the absence of liquid in the sample tube.

26 Claims, 9 Drawing Sheets

FIG. 5
DUTY CYCLES .20-.50, NARROW FILTER

FIG. 6
DUTY CYCLE=.20, WIDE FILTER

GAS BUBBLE DETECTOR

GOVERNMENT RIGHTS

The invention described herein was made in the performance of work under NASA contract No. NAS 8-50000 and is subject to the provisions of the National Aeronautics and Space Act of 1958 (42 U.S.C. 2457).

BACKGROUND OF THE INVENTION

FIELD OF INVENTION

This invention relates to gas bubble detectors and is specifically directed to the detection of bubbles in a flowing stream of liquid, the minimum detectable size being smaller than was possible with prior art techniques.

This invention will be described in connection with the detection of air bubbles in a flowing stream of water in a zero gravity environment where this invention is quite advantageous but it is to be understood that this invention is usable to detect such air bubbles at earth gravity and other gas bubbles in other liquids at zero and earth gravity.

Specifications for potable water purity for use by man when functioning in a zero gravity environment must include a maximum limit on free gas in the water because of the adverse physiological effects produced. When more than a minimal amount of free gas, such as air, is ingested, the zero gravity environment greatly increases stress on the digestive system caused by the ingested gas, resulting in severe pain.

PURPOSE OF THE INVENTION

A gas bubble detector was needed to analyze a sample of approximately 0.5 to 1.0 liter of processed water at a flow rate of 30 ml/min, to measure the total undissolved gas, and to provide an output signal proportional to the gas volume in the sample. The maximum allowable undissolved gas per sample was no more than 0.01% by volume, with an analytical range of 0.0 to 1.00% by volume, and a precision of ±0.005%. The calculated minimum possible diameter of a gas bubble in water is approximately 0.01 cm or about 0.004 inch diameter, or a volume of about 0.0005 microliter.

Conventional methods of gas bubble detection generally employ ultrasonic or optical methods.

Ultrasonic Method The ultrasonic method generally depends upon the principle that ultrasonic energy is transmitted through water with less transmission loss than through air. A commonly used ultrasonic frequency is 2 MHz, which is low enough to afford reasonable penetration depth, and high enough to afford reasonable resolution. Penetration depth decreases with increasing frequency, and resolution increases with increasing frequency. The resolution, or the smallest gas bubble detectable in water, depends upon the wavelength of the sound wave in water. The relation between wavelength, sound velocity, and frequency is $$\lambda = \frac{c}{f} \text{ cm}$$

Solving eq. 1 for wavelength of sound in water where f=2 MHz, and c=1.43E5 cm/s, we obtain $$\lambda = \frac{1.43E5}{2E6} = .0715 \text{ cm} = .029 \text{ inch} \quad (2)$$

which is about seven times higher than the desired minimum detectable bubble diameter-a distinct disadvantage. The volume of a 0.029" dia bubble is about 0.2 microliter, or about 400 times larger volume than the minimum required detectable volume. A second disadvantage of the ultrasonic method is that detection of a gas bubble depends upon a decreasing ultrasonic signal. The preferred method would provide an increasing output signal when a gas bubble is detected.

Optical Methods Optical methods for detecting gas bubbles in water generally depend either upon the absorption or refraction of light by the water, there being less absorption of light when gas is present, or an altered refracted light path when gas is present. Normally, the minimum volume of free gas detectable from a conventional optical bubble sensor is between 1 and 0.1 microliter. Since a volume of a 0.004" dia. bubble is about 0.005 microliter, an improved detection method was required.

It is therefore an object of this invention to improve the prior art and to provide the following:

1. A gas bubble detector which detects bubbles in a flowing stream of water, the minimum detectable bubble size being considerably smaller, eg, in the order of 0.004 in, than was possible with previous techniques.
2. A gas bubble detector which employs a small incandescent filament as an IR source whose intensity is modulated at a frequency in the vicinity of 1 kHz to 3 kHz and a pulse duty cycle of approximately 20%, so that an optimum ratio of absorbed to transmitted light is obtained when water versus air is present in the sample tube.
3. A gas bubble detector which uses a venturi to improve the ability of the sensor to detect small bubbles.
4. A gas bubble detector demodulation method which derives a time-varying vector magnitude signal proportional to the area of the detected gas bubble.

SUMMARY OF THE INVENTION

A gas bubble detector having a modulated IR source focused through a bandpass filter onto a venturi, formed in a sample tube, to illuminate the venturi with modulated filtered IR to detect the presence of gas bubbles as small as 0.01 cm or about 0.004" in diameter in liquid flowing through the venturi. Means are provided to determine the size of any detected bubble and to provide an alarm in the absence of liquid in the sample tube.

DETAILED DESCRIPTION OF INVENTION (and the rationale of its development).

An optical method was chosen since, unlike ultrasonic energy, optical wavelengths are small compared to the dimensions of the minimum bubble size to be detected.

Figure 1:
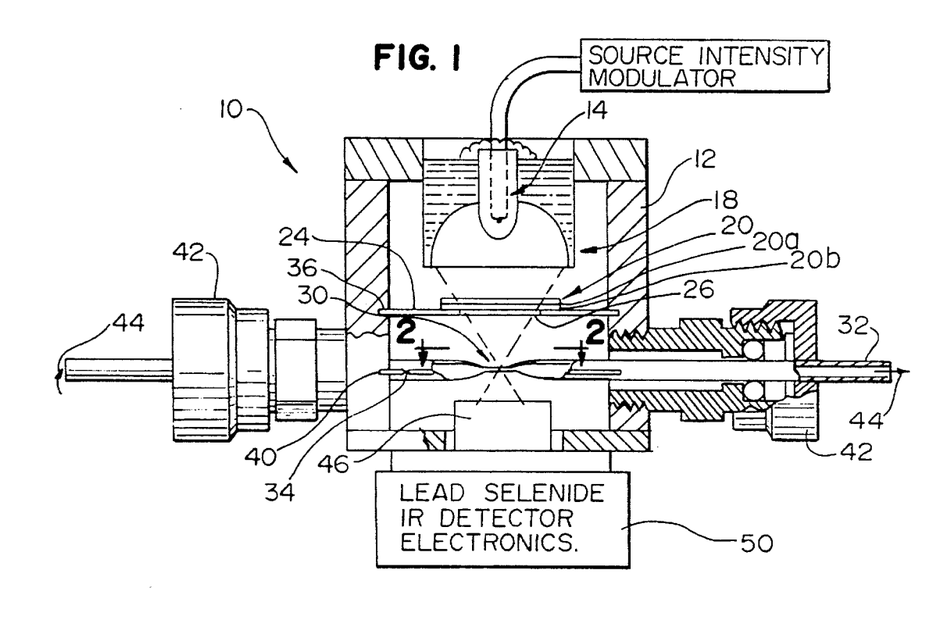
FIG. 1 is a schematic cross-sectional view, in elevation and partially broken away, of a gas bubble detector of this invention.
Figure 2:
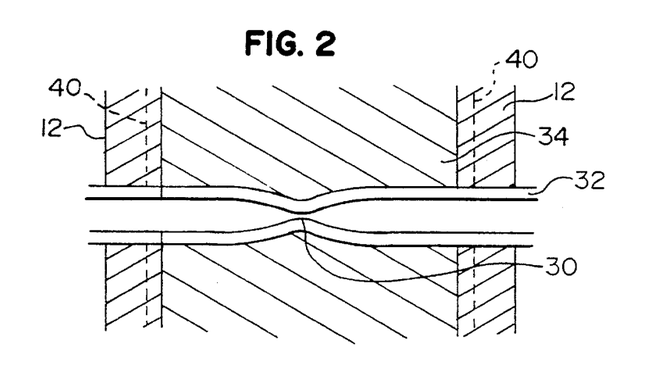
FIG. 2 is a plan view of a fitted mask, taken along 2—2 of FIG. 1.
Figure 3:
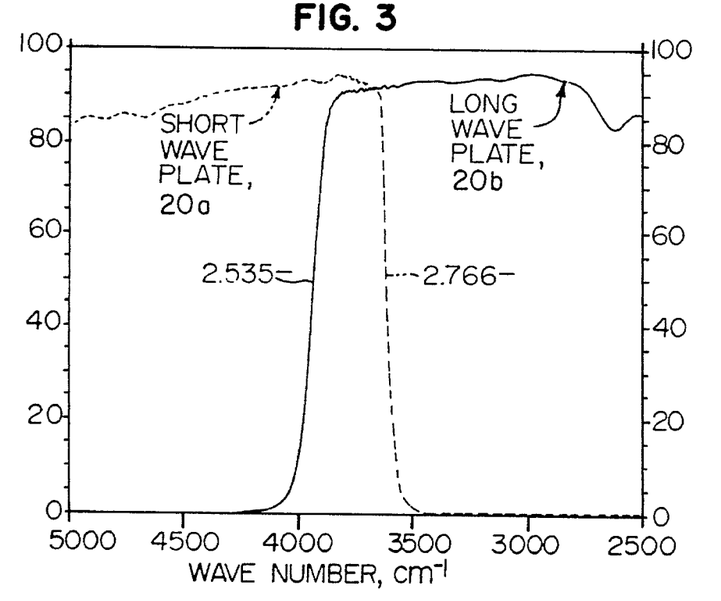
FIG. 3 is a graph showing the response of an IR Bandpass filter between 3500 and 4000 cm$^{-1}$.

FIGS. 1 and 2 show the construction of the gas bubble detector 10 of this invention. The gas bubble detector 10 comprises a housing 12 forming an enclosure in which an incandescent lamp 14 is used as a modulated IR source. The lamp 14 is connected to a source intensity modulator 16. A suitable reflector 18, preferably parabolic, focuses the output of the lamp 14 through a bandpass filter 20 supported on a glass plate 24. The bandpass filter 20 comprises two plates, a lowpass filter 20a and a highpass filter 20b, whose response are shown superimposed to form a bandpass filter as shown in FIG. 3.

The glass plate 24 has an opening 26 through which the focused IR energy passes to illuminate a venturi 30 formed in part of a glass tube 32. The illuminated venturi 30 is also referred to as the sample area. The glass tube 32 and venturi 30 have a fitted opaque mask 34, as shown in FIG. 2, to block stray light within the housing 12. The glass plate 24 and mask 34 are affixed within the housing 12 by any suitable means, such as by slots 36 and 40.

The glass tube 32 is held and sealed with respect to the housing 12 by a pair of compression fittings 42 which are conventional and commercially available. The material of the glass tube 32 is a special glass formulated to have a low attenuation of IR energy which is readily available from commercial sources. The illumination of the venturi 30 by the focused IR is to detect bubbles in the fluid flowing through the venturi 30 represented by arrows 44. The change in IR energy when a bubble is present in the fluid is detected by an Pb—Se IR detector 46 and associated electronics 50, both of which are also commercially available as a unit.

The principle of operation is to illuminate the flowing sample of water with infrared energy within the infrared absorption band from 2.5 to 2.8 microns and detect the transmitted light with a sensitive IR detector, such as 46. When an air bubble enters the illuminated area, a greater amount of light energy is sensed by the detector 46 due to the reduction in the amount of water present, causing an increase in transmitted light. FIG. 3 is an infrared spectrogram of the bandpass filter comprising a short wave plate 20a and a long wave plate 20b showing that the filter will pass only energy which lies within the absorption band of water 3500–4000 cm$^{-1}$, maximizing the ratio of the signal through air in the sample tube to the signal through the fluid to thus give a better signal-to-noise ratio.

As in many conventional non-dispersive IR analyzers, due to AC coupling of the signal from the detector to the preamplifier, the IR energy must be intensity modulated when passing through the sample, and then the resulting AC signal must be demodulated to recover a steady-state representation of the absorptivity of the sample. Conventional non-dispersive IR analyzers commonly use a motor-driven chopper to intensity modulate the light from the infrared source. In order to increase the system reliability, instead of using a motor-driven chopper, a miniature incandescent lamp filament is utilized, which may be electrically intensity modulated at a rapid rate due to its low thermal mass. Optimum frequency and duty cycle were chosen experimentally to obtain the maximum ratio of output signal with air versus with water present inside the sample tube. The optimum frequencies is a function of the bandpass filter, the glass tube and other factors.

Several improvements were made to increase the sensitivity of the system, including 1. Modification of sample tube by forming a venturi in the area of the IR focal point,
2. Optimizing filament modulation duty cycle and power level for maximum ratio of IR energy with water versus air in the sample tube,
3. Optimizing modulation frequency for maximum speed of response while retaining adequate signal-to-noise ratio.
4. Development of a demodulation scheme which enhances the detection sensitivity by deriving a time-varying vector magnitude proportional to the area of the gas bubble passing through the sample tube.

1. Sample Tube With Venturi Modification The original sample tube was 1 mm I.D. and 3 mm O.D., and minimum detectable bubble size was approximately the same as the I.D. of the tube (1 mm, or 0.039"). The venturi 30 was formed in the glass tube 32 as shown in FIG. 2 to provide a venturi I.D. of about 0.015". The minimum detectable bubble size decreased to approximately 0.004". The increased sensitivity was due to (1) the smaller I.D. giving a larger ratio of light transmitted through bubbles smaller than 0.015" dia. versus light transmitted through a water sample with no free air present, (2) the decrease in pressure (Bernoulli effect) producing an enlarging of the bubble size in the sample area, and (3) less bypassing of the IR energy through the thinner wall of the glass tubing. The pressure drop across the venturi was 1.5 PSI, which was not excessive, since the system operating pressure was 25 to 50 PSI.

2. and 3. Optimization of IR Source Duty Cycle and Modulation Frequencies

Figure 4:
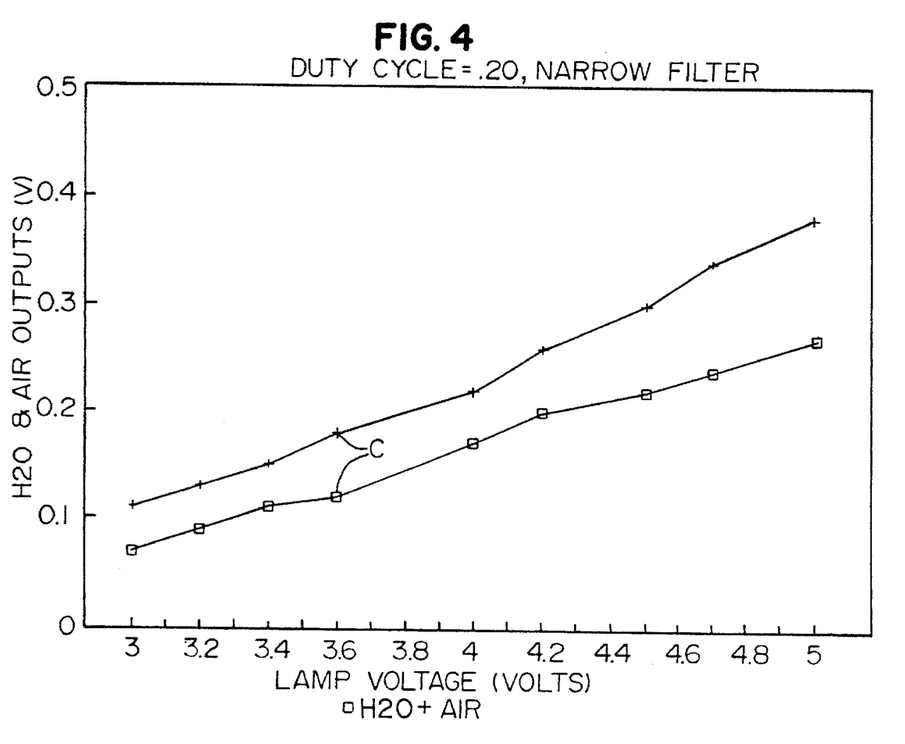
FIG. 4 is a graph comparing water and air output versus lamp voltage.
Figure 5:
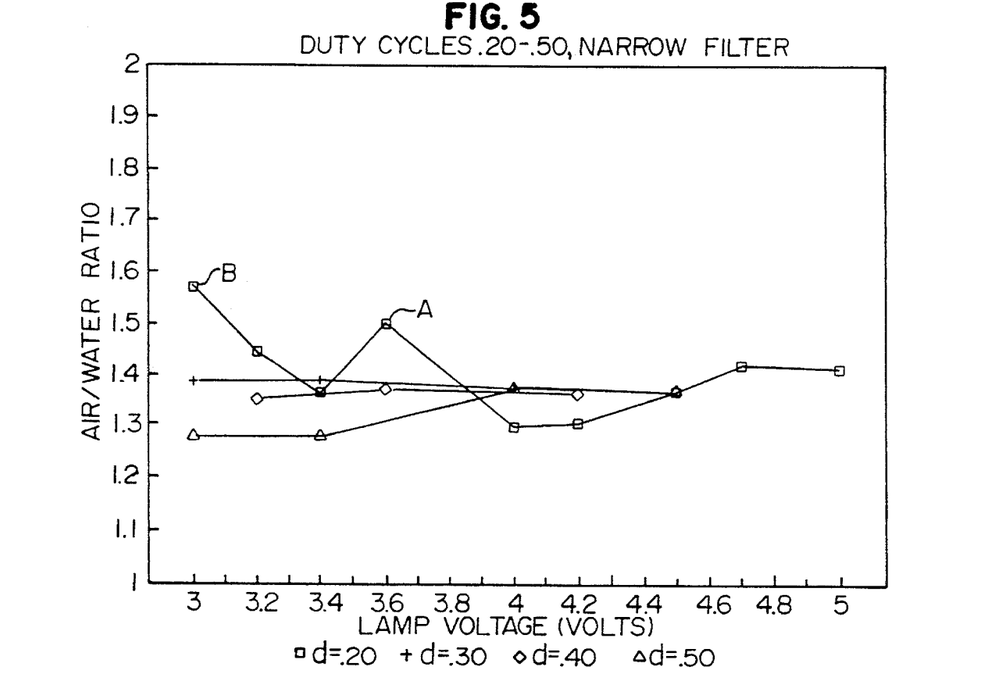
FIG. 5 is a graph comparing air/water ratio output signal versus lamp voltage at various duty cycles.
Figure 6:
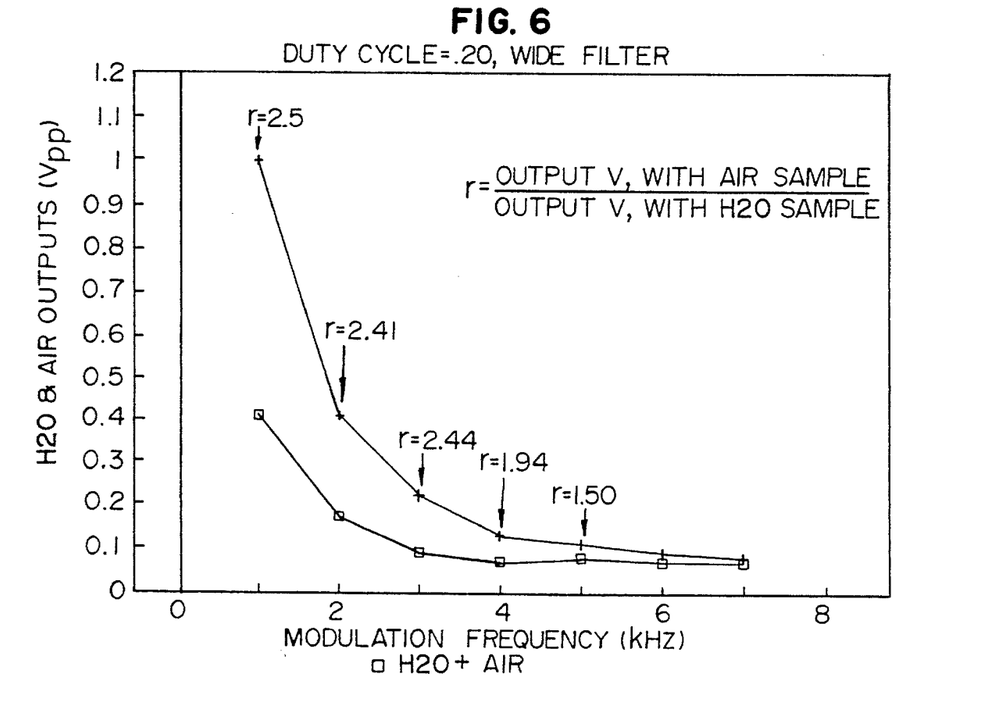
FIG. 6 is a graph comparing water and air output signal versus modulation frequency at a duty cycle of 0.20.

The percent duty cycle of the electrical current pulse used to heat the filament, and the lamp power level, were both found to be critical variables in the optimization of the ratio of detected signal with and without air in the sample tube. A third variable, the modulation frequency, must also be chosen carefully, because of the very short time a small bubble is present in the sample area; i.e., at least one cycle of the modulation frequency should be completed during the time the smallest bubble is present in the sample area. Turning now to FIGS. 4–8 it can be seen that FIG. 4 is a plot of air and water signal amplitudes vs lamp voltage at a duty cycle of 0.20, FIG. 5 is a plot of air/water output ratio output signal vs lamp voltage at various duty cycles, and FIG. 6 is a plot of water and air output signals vs frequency at a duty cycle of 0.20. The operating frequency was chosen to be 3 kHz since that was the highest frequency at which signal-to-noise ratio was still acceptable.

From FIG. 5, it can be seen that the optimum duty cycle for the filament current was found to be 0.20 (20% on and 80% off), point A, since the highest air-to-water signal ratio was found at this value. FIG. 5 shows that the air-water ratio output signal peaks at a lamp voltage of 3.6 volts (still higher at 3.0 volts, point B, but FIG. 4 shows higher signal-to-noise ratio at 3.6 volts, point C); therefore, the operating point chosen was at a lamp voltage of 3.6 volts and duty cycle of 0.20.

Figure 7:
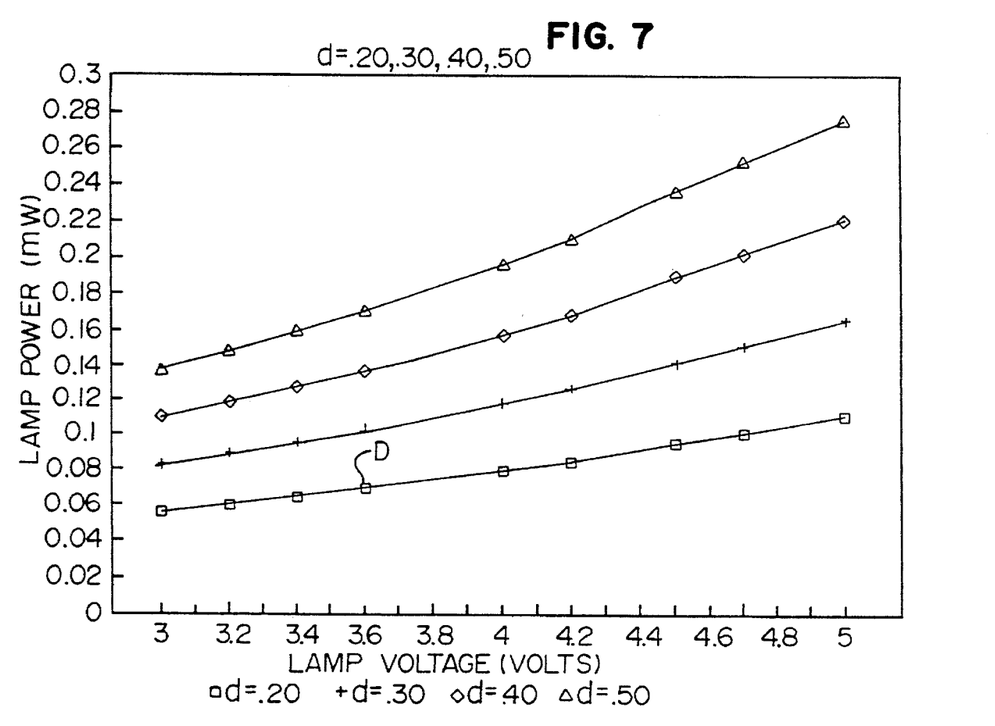
FIG. 7 is a graph comparing lamp power versus lamp voltage for various duty cycles.
Figure 8:
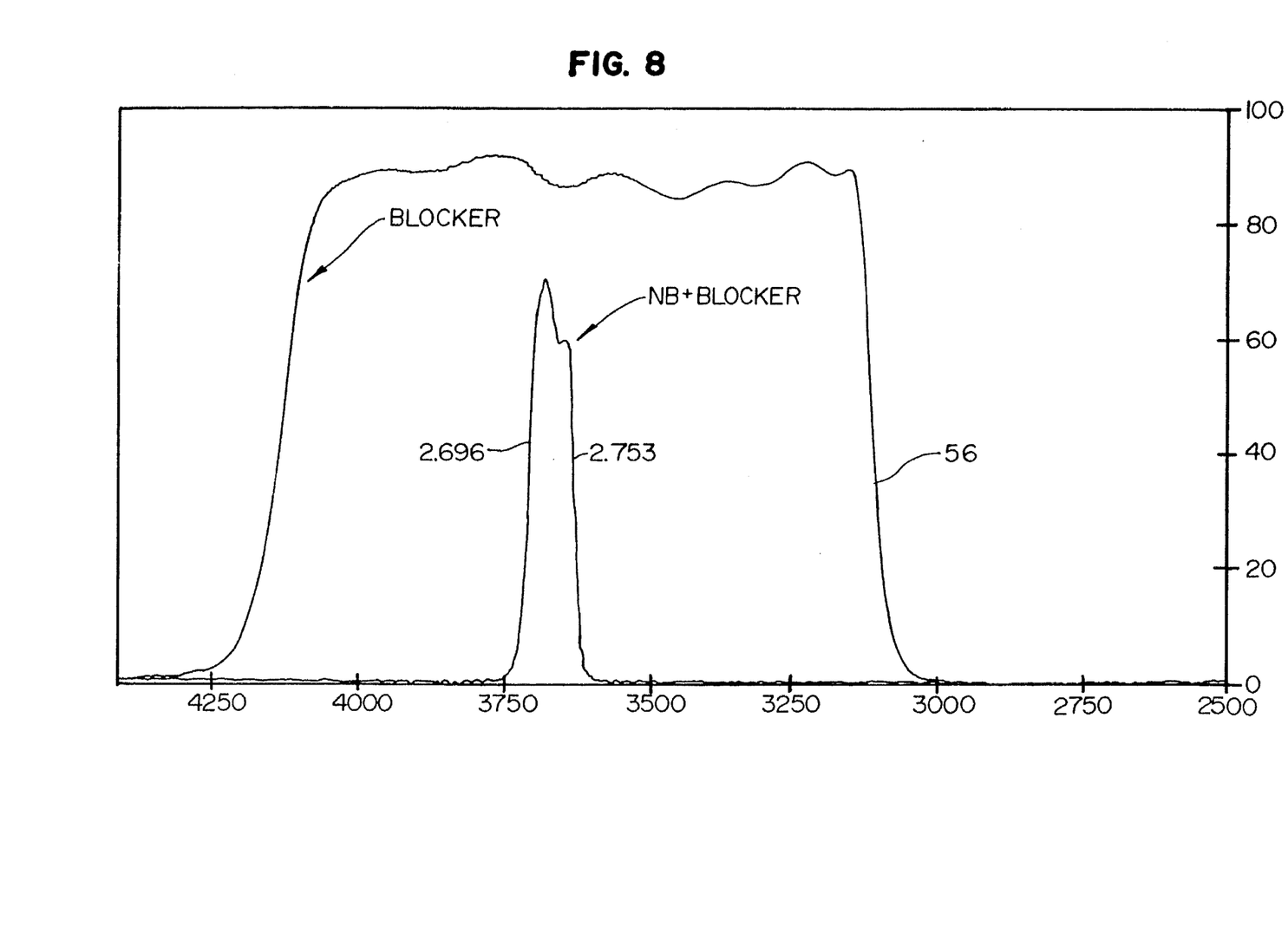
FIG. 8 is a graph comparing an interference filter and a Pb-Se blocker superimposed.

FIG. 7 is a plot of lamp power vs lamp voltage for various duty cycles. FIG. 8 is an interference filter with a Pb—Se blocker 56 superimposed to make the IR detector 46/50 non responsive to any other energy than that allowed through the filter.

FIG. 7 shows that at a duty cycle of 0.20 and lamp voltage of 3.6 volts, the lamp power is about 65 milliwatts, point D, which causes the lamp to glow a dull red color, indicating that the filament is not operating at a high enough temperature to cause reliability problems.

The data shown in FIGS. 4 and 5 were taken with an IR interference filter installed which had the characteristics shown in FIG. 8, and before the sample tube 32 was modified with the venturi 30 in the sample area. The data shown in FIG. 6 were taken with an IR bandpass filter 20 installed which had the characteristics shown in FIG. 3, after the venturi 30 was added. The bandpass filter bandwidth was four times wider than the interference filter, resulting a signal amplitude increase of about 4:1. The improved air/water ratios shown in FIG. 6 are primarily due to the wider bandpass filter. Adding the venturi 30 enabled detection of the smaller bubble sizes.

4. Demodulation Method

The commonly accepted method of demodulation of the detected IR energy is to detect amplitude changes due to the increased transmission when air is present in the sample tube 32. This method is satisfactory when the bubble of air is present inside the sample tube 32 for several cycles of the modulating frequency. When a very small bubble must be detected in flowing fluid, the bubble may exist in the sample tube 32 for one cycle or less of the modulating frequency. For example, with the fluid flowing at 30 ml/min and a sample tube I.D. of 1 mm, the fluid velocity is $$\text{velocity} = \frac{\text{flowrate (ml/min)}}{\text{area (cm}^2\text{)} \times 60} \text{ cm/sec} \quad (3)$$

If the fluid flows at a rate of 30 ml/min and the sample tube I.D. is 0.015" the fluid velocity is, from eq. 3

$$v = \frac{30}{60\pi \frac{(.015 \times 2.54)^2}{4}} = 439 \text{ cm/sec} \quad (4)$$

Assume a 0.015" dia. bubble passes through the sample tube without volume expansion due to reduced pressure in the venturi 30. The time for the bubble to pass through the sample area is $$t = \frac{x}{v} = \frac{.015 \times 2.54}{429} = 8.9E\text{-}5 \text{ sec, or 89 } \mu\text{sec} \quad (5)$$

If the modulation frequency is 3 kHz, the period is 1/(3 kHz), or 333 microseconds. The portion of a cycle occupied by a 0.015" dia bubble moving through the sensor at 429 cm/sec is then 89/333, or 26% of one cycle. Amplitude detection of the change in output produced from this amount of modulation would be difficult to detect by simple amplitude detection. A bubble diameter of the minimum size specified (0.004") would occupy only about 6% of one cycle of modulation, and would be even more difficult to detect (volume expansion of the bubble due to decreased pressure in the venturi 30 may increase the time that the air is present in the sample area).

Figure 9:
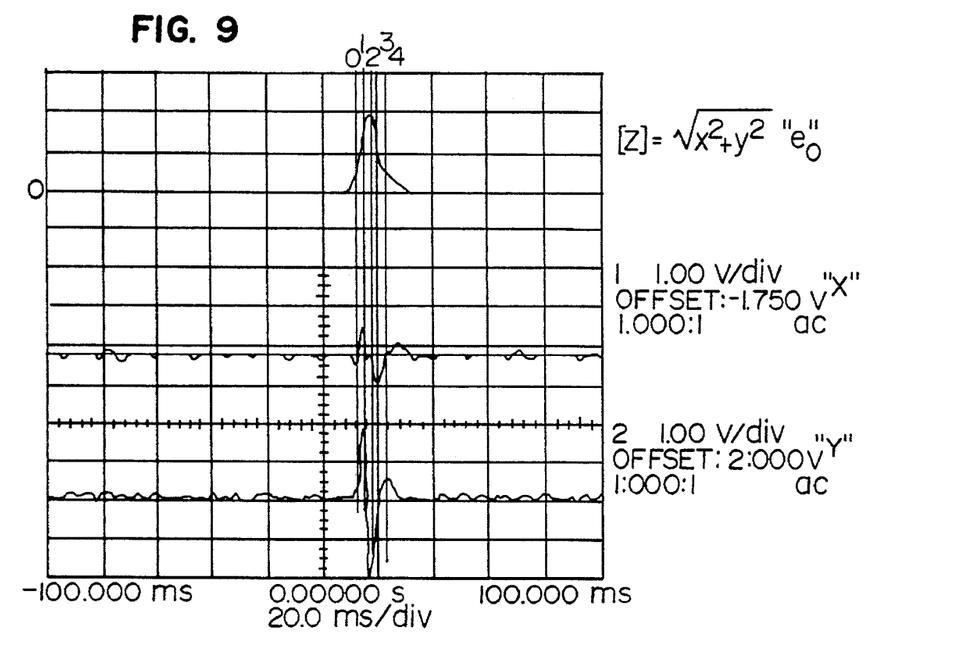
FIG. 9 shows a graph with channel 1, "x" demodulated signal; channel 2, "y" demodulated signal; and a construction $|z|=\sqrt{x^2y^2}$.

Referring now to FIG. 9, by using a vector demodulation process similar to that employed by commonly used instruments called lock-in amplifiers, the x (Ch1) and y (Ch2) components of the vector, which results from the IR energy transmission being enhanced by the momentary presence of air in the sample area, can be elicited or demodulated. The time-varying absolute magnitude of the x and y components is then calculated. In the example of FIG. 9, the vector magnitude was calculated graphically, but analog circuitry hereinafter discussed make this calculation continuously.

The calculation consists of (1) Synchronous demodulation of the detector output using the 3 kHz modulation frequency as one reference and a 90-degree phase-shifted 3 kHz modulation frequency as a second reference, which produces x and y components (this is equivalent to processing by the lock-in-amplifier), (2) Restoring the baseline to zero (equivalent to removing the carrier term), and (3) Computing the absolute magnitude vector continuously at every point along the x and y waveforms using an analog vector resolution circuit.

The foregoing procedure will detect bubbles which are of short time duration. For detecting gas which exists in the sample area for a relatively long time, steady-state increase in signal is determined by sensing a change in signal amplitude which exists for time period longer than a few modulation cycles, using an amplitude modulation detector and a comparator.

Figure 10:
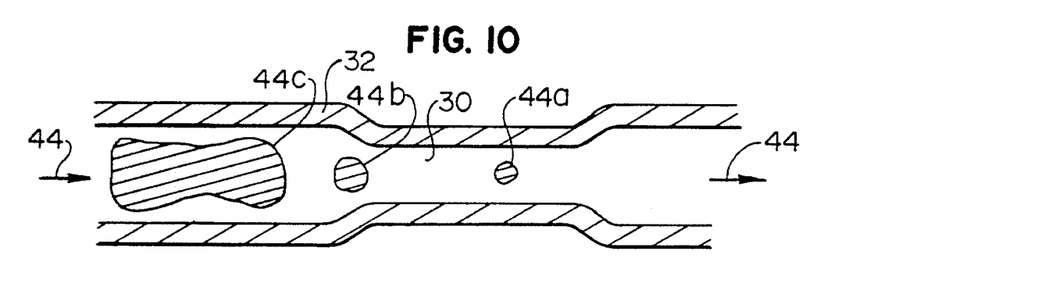
FIG. 10 is an enlarged view of the tube and venturi of FIG. 1 showing gas bubbles of varying sizes in the liquid flow.

Reference is now made to FIGS. 10–17. FIG. 10 is an enlargement of the sample tube and shows the venturi 30 and the flow of fluid 44 with two different sizes of small bubbles 44a and 44b and a large bubble 44c.

Figure 11:
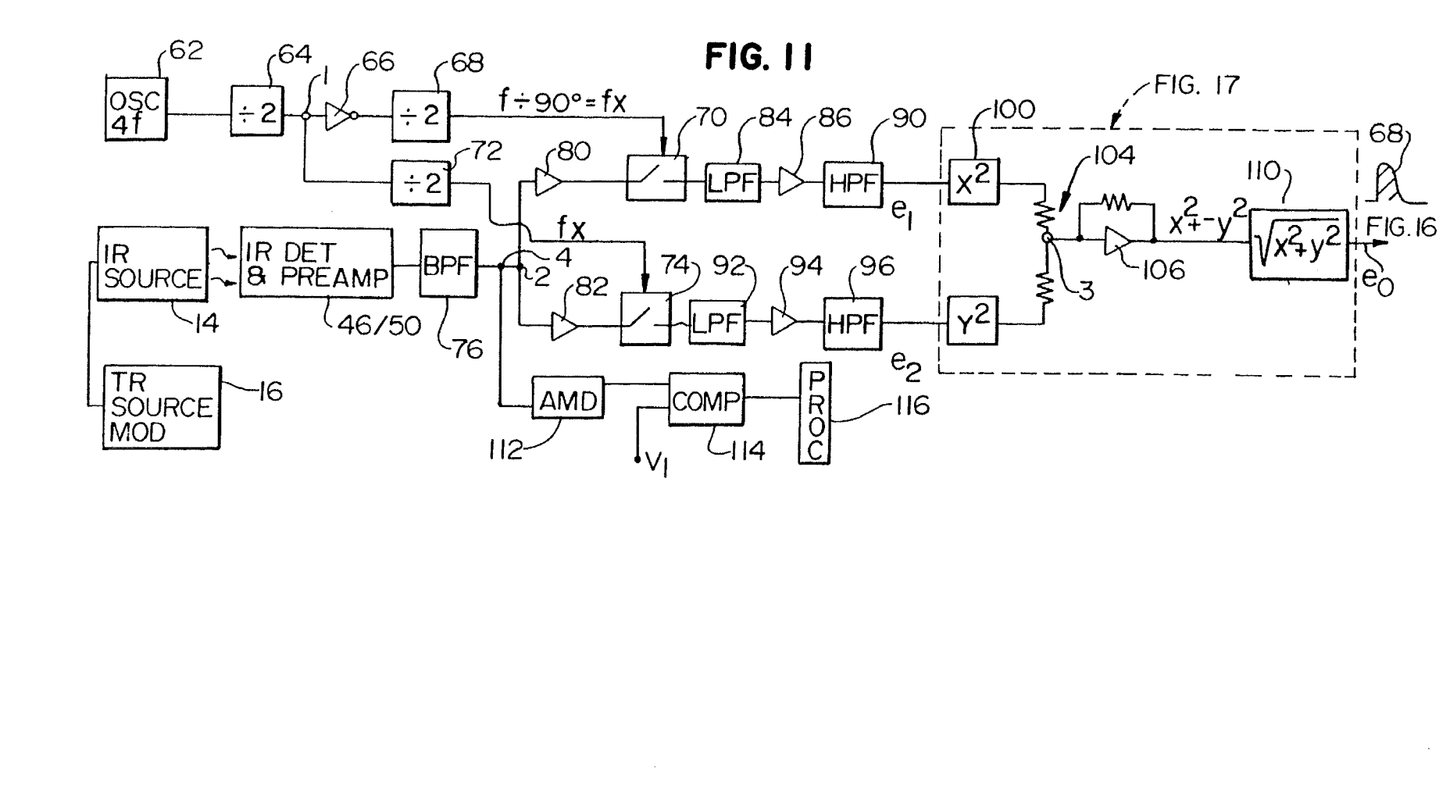
FIG. 11 is a schematic of a demodulator and preprocessor circuit to produce the output $|z|= \sqrt{x^2y^2}$.
Figure 12:
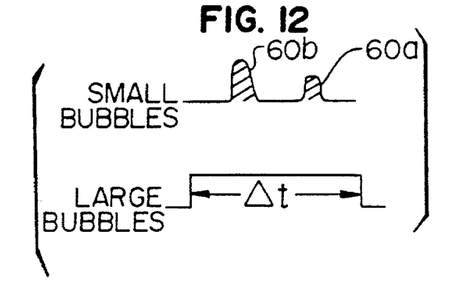
FIG. 12 is a profile of the output signals of small and large gas bubbles as shown at the two outputs in FIG. 13 is a timing diagram of the circuit of FIG. 11.

The output of the demodulator and preprocessing circuitry of FIG. 11 will produce a waveform, such as 60, for the different sizes of bubbles. As shown in FIG. 12, waveform 60a represents the area of the smallest bubble 40a and waveform 60b represents the area of the larger small bubble 40b. The area of the pulse waveform represents the area of a detected bubble, and an area-to-volume calculation may be performed based upon calibration of the system with bubbles of known volume. The two different sizes of small bubbles and the detection of the large bubble over time Δt is shown in FIG. 12.

The demodulator and preprocessor circuitry of FIG. 11 comprises an oscillator 62 operating at 4× the desired frequency and is connected to a divide-by-2 counter 64 whose output is connected at node 1 to an inverter 66 and to a second divide-by-2 counter 68 to provide the frequency f-90°=fx. The output fx is connected to a switch 70. A second divide-by-2 counter 72 is connected at node 1 to provide frequency fy and which is connected to another switch 74.

Figure 13:
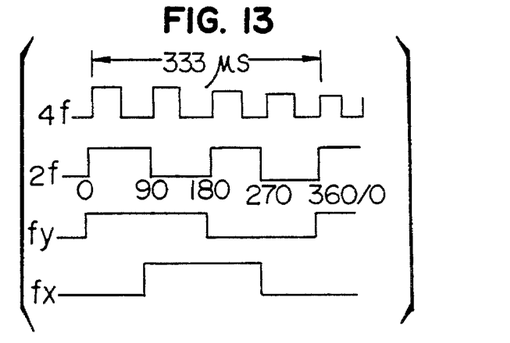

FIG. 13 shows the timing diagram in which the original oscillator frequency is divided to form frequencies fx and fy.

Another branch of the circuit of FIG. 11 comprises the IR source 14 as detected by the IR detector and electronics 46/50 (FIG. 1) which in turn is connected to a bandpass filter 76. The IR source intensity is modulated by the IR source modulator 16.

The output of the bandpass filter 76 is coupled at node 2 to circuitry to detect small bubbles and is coupled at node 4 to circuitry to detect large bubbles.

Thus, to detect small bubbles, the output of the bandpass filter 76 is coupled to the switches 70 and 74 through a pair of operational amplifiers 80 and 82 which function as buffers. The output of switch 70 is connected to lowpass filter 84, to a buffer amplifier 86 and then to a highpass filter 90. The output of filter 90 is designated as $e_1$. The output of switch 74 is connected to a second lowpass filter 92, to a second buffer amplifier 94 and then to a second highpass filter 96. The output of filter 96 is designated as $e_2$. The highpass filters 90 and 96 remove the DC level which results from demodulation of the unmodulated carrier, thus "restoring" the baseline, or zero reference, of the demodulated signal which resulted from a bubble interrupting the optical path.

The output $e_1$ is multiplied at multiplier 100 to provide $x^2$ and the output $e_2$ is multiplied at multiplier 102 to provide $y^2$. The output of these two multipliers are connected at node 3 between a voltage divider network 104 and through an inverter 106 to provide an output $x^2+y^2$. This output is connected to a divider 110 to provide the square root of $x^2+y^2$ which is the output $e_o$, waveform 60.

Figure 17:
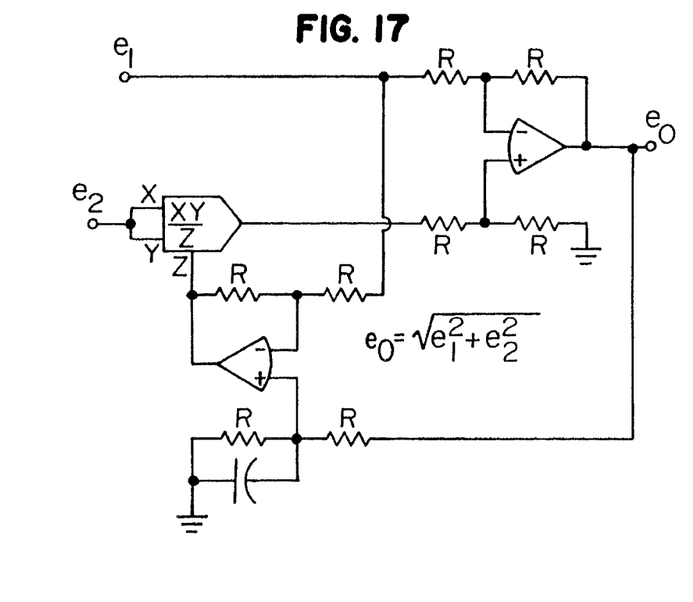

The circuitry for squaring the x and y components, adding the $x^2$ and $y^2$ components and taking the square root of the sum of $x^2$ and $y^2$ is shown in FIG. 17 and is a commercially available analog multiplier chip connected as a square root circuit.

To detect large bubbles, the output of the bandpass filter 76 is connected at node 4 to an amplitude modulation detector 112 whose output is connected to one input of a comparator 114. The other input to the comparator is connected to a reference voltage $V_1$. The output of the comparator 114 is connected to a processor 116, which is also connected to the post processor circuitry of FIG. 16 to be described.

Figure 14A:
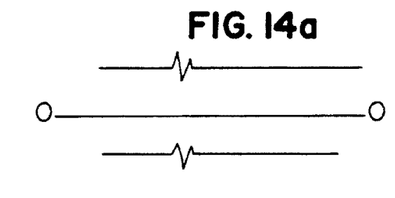
FIG. 14 shows the output of a small bubble and the output signals processed by the circuit of FIG. 11.
Figure 14B:
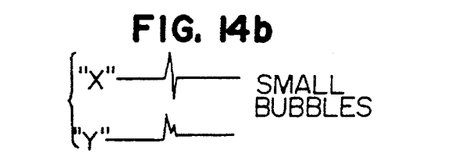
Figure 14C:
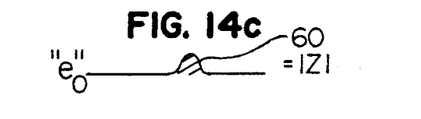

Taking FIGS. 12, 14 and 15 together, there is shown the output of the bandpass filter 76 as processed by the remainder of the circuit of FIG. 11. FIG. 14 and particularly FIG. 14a, shows the output of the bandpass filter 76, with a small bubble being detected in the venturi 30 changes in the amplitude of the modulation frequency which are processed by the circuit of FIG. 11 to form the x and y signals as they would appear at the output of the highpass filters 83 and 84, $e_1$ and $e_2$, respectively. These signals are processed to form the output signal $e_o$, FIG. 14c. The processing of these signals correspond to the signals of FIG. 9. Channel 1 corresponds to x of FIG. 11, channel 2 corresponds to y of FIG. 11 and z corresponds to the output $e_o$ of FIG. 11.

Figure 15A:
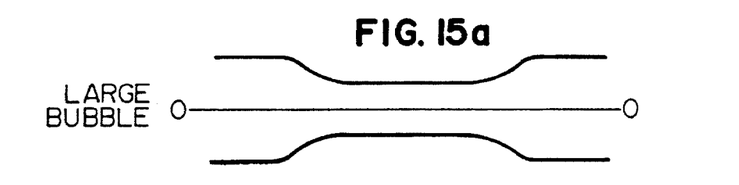
FIG. 15 shows the output of a large bubble and the output signals processed by the circuit of FIG. 11.
Figure 15B:
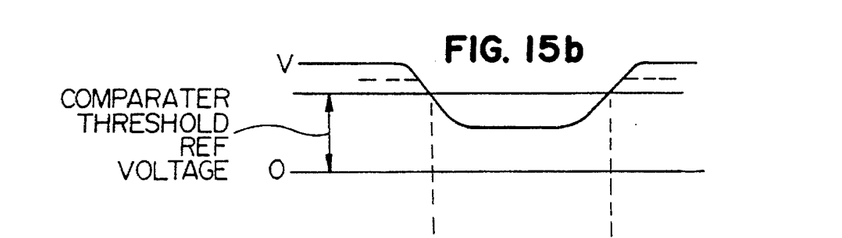
Figure 15C:
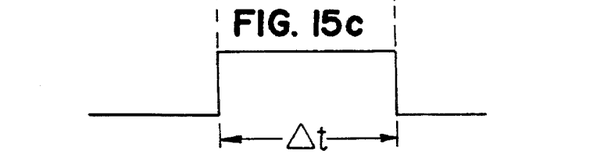

FIG. 15 shows the modulation frequency at the output of the bandpass filter 76 where a large bubble is being detected in the venturi 30. This large bubble causes a large decrease in the amplitude of the modulation frequency extending over several cycles as in FIG. 15a which is detected by the amplitude modulation detector 112 and compared in the comparator 114 with the threshold voltage reference $V_1$ which produces an output signal $\Delta t$ corresponding to the length of time the amplitude of the envelope is below the threshold voltage. The detection of this large bubble is sent to the processor 116. The time width $\Delta t$ is measured by the processor 116 and converted into gas volume, knowing the flow velocity and the ratio of the diameter of the flow tube 32 to the diameter of the venturi 30. If the time $\Delta t$ is exceedingly long, the processor may provide an alarm indicating no fluid in the system.

Figure 16:
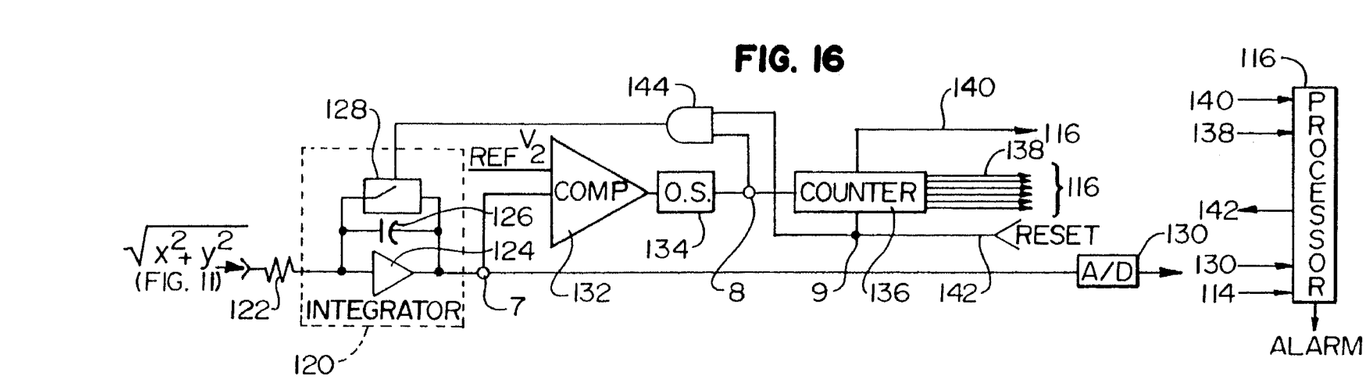
FIG. 16 is schematic diagram of a post processor circuit to process the output signal of the circuit of FIG. 11 and, FIG. 17 is a schematic diagram of an analog circuit for vector magnitude computation.

FIG. 16 illustrates the post processor circuit for processing the output from the circuit of FIG. 11. The output of the circuit of FIG. 11 is connected at node 5 to the input of an integrator 120 through a resistor 122. The integrator 120 includes an operational amplifier 124, an integrator capacitor 126 connected across the operational amplifier and an integrator reset switch 128 connected across the capacitor 126. The output of the integrator 120 is also connected, 1), to an analog-to-digital converter 130 and to processor 116 (see also FIG. 11) and, 2), at node 7 to one input of a comparator 132 whose other input is connected to a reference voltage $V_2$. The output of the comparator 132 is connected to a one-shot multivibrator 134 the output of which, in turn, is connected at node 8 to a counter 136. The output of the counter 136 is in parallel as at 138 and connected to a data bus (not shown) of processor 116. The counter 136 has another output connected to an overflow signal line 140 which, in turn, is connected to the data bus of processor 116. This latter overflow signal line 140 is activated when the counter reaches maximum possible count (ie, $2^{16}$ for a 16 bit counter) for a small bubble and signals the presence of a large bubble and/or no fluid in the sample area. The overflow signal line 140 may be connected to activate an alarm. The counter 136 is connected at node 9 to a reset input 142. Reset input 142 is also connected to an AND gate 144 at node 9. The other input to the AND gate 144 is connected at node 8 to the output of the multivibrator 134. The output of the AND gate 144 is connected to the switch 128.

The output of the comparator 132 resets the output of the integrator 120 to zero when the integrator output increases above a maximum voltage, which is determined by the reference voltage $V_2$. The integrator output voltage is limited to a maximum value determined by the integrator power supply (not shown). If the output of the integrator 120 were allowed to exceed this voltage, the output would become saturated and would no longer be useful for indicating the volume of the gas bubbles. The one-shot multivibrator 134 develops a pulse of sufficient time to allow the reset switch 128 to fully discharge the capacitor 126 of the integrator 120. Whenever a small bubble is detected, the output voltage of the integrator 120 will increment a small amount, proportional to the area of the bubble. The integrator output voltage is connected to the A/D converter 130 to enable the integrator output to be sampled periodically by the processor 116 where the information is converted into a history of the size of each bubble which was detected and when it was detected. The output of counter 136 represents the total number of times the integrator 120 was reset, which corresponds to the total area of bubbles measured, starting at the time the counter 136 was reset to zero.

Normally the processor 116 would read the output of the counter 136 periodically, and then resets it by a pulse on line 142. If an overflow signal on line 140 is presented to the processor 116, this signal is read by the processor 116 on a priority interrupt and then the processor 116 will reset the counter 136 as before.

We claim:

1. An apparatus for detecting gas bubbles in a flowing liquid comprising:

a venturi formed in a tube through which liquid flows, a modulated IR energy source directed onto the liquid flowing through said venturi, means for detecting the amount of IR energy absorbed by said liquid and by any gas bubbles in said liquid and providing an output signal proportional to the amount of IR energy absorbed, and means for processing said output signal to determine the size of any gas bubble in said liquid as a function of the amount of energy absorbed and time.

2. The apparatus as claimed in claim 1 wherein said means for processing said output signal includes alarm means for emitting a signal indicating that a large gas bubble is present or that there is no liquid in the tube or venturi.

3. The apparatus as claimed in claim 1 further including an optical filter which filters the modulated IR energy into wavelengths corresponding to the absorption characteristics of the liquid flowing through the venturi.

4. The apparatus as claimed in claim 3 wherein said optical filter is a bandpass filter.

5. The apparatus as claimed in claim 1 wherein said modulated IR energy source comprises a frequency modulated incandescent lamp operating at a selected duty cycle.

6. The apparatus as claimed in claim 5 further including a reflector for focusing the output of said incandescent lamp onto the liquid within said venturi.

7. The apparatus as claimed in claim 5 wherein the voltage applied to said incandescent lamp is approximately 3.6 v and the duty cycle of said incandescent lamp is approximately 20% when the liquid is water and the gas is air.

8. The apparatus as claimed in claim 1 wherein said means for processing said output signal comprises circuitry which derives a time-varying vector magnitude signal proportional to the size of any detected gas bubble in said flowing liquid.

9. A gas bubble detector which detects bubbles as small as 0.004 inches in a flowing stream of liquid comprising:

a housing, a source of IR energy, means in said housing directing said IR energy to a focal point, means between said source and said focal point for filtering said IR energy to a bandwidth corresponding to the absorption capabilities of said liquid, tube means in said housing capable of handling said flowing liquid, a venturi formed in said tube means and located at said focal point, an IR detector means located so as to detect the amount of IR energy absorbed by said flowing liquid and any gas bubble in said flowing liquid and to provide an output signal, and means for processing the output signal from said detector means so as to determine the number and size of any gas bubbles in said flowing liquid.

10. The detector as claimed in claim 9 wherein said means directing said IR energy is a parabolic reflector.

11. The detector as claimed in claim 9 wherein the internal diameter of said venturi is approximately 0.015 in.

12. A method of detecting gas bubbles in a flowing liquid comprising the steps of:

providing a flow of said liquid which may contain one or more gas bubbles through a venturi, directing IR energy towards said venturi so as to illuminate said venturi and the liquid and gas flowing therethrough, filtering said IR energy as it is being directed toward said venturi to correspond to the absorption characteristics of the liquid and gas flowing through said venturi, providing detector means for absorbing said IR energy in said venturi and for producing an output signal proportional to the absorption of the IR energy of said liquid and gas flowing through said venturi, and processing said output signal to determine the size of any detected gas bubble in said flowing liquid.

13. The method as claimed in claim 12 wherein said step of processing said output signal includes the step of determining the size and number of gas bubbles in said flowing liquid.

14. The method as claimed in claim 12 wherein said step of processing said output signal also includes the step of determining when a large bubble or no fluid is present in said venturi.

15. An apparatus for detecting gas bubbles in a liquid flowing through a sample tube comprising:

a sample area comprising a venturi formed in said sample tube through which liquid flows;

an IR energy source directed onto the liquid flowing through said sample area;

frequency modulation means for modulating the intensity of IR energy that is directed onto the sample area by said IR energy source at a selected duty cycle; and an IR detector for sensing the IR energy incident to said detector and providing an output signal that is proportional to the amount of IR energy absorbed by the liquid flowing through said sample area;

wherein the selected duty cycle of said IR energy source is approximately 20% when said apparatus is detecting air bubbles and said flowing liquid is water.

16. The apparatus as claimed in claim 15 wherein said IR energy source comprises an incandescent lamp.

17. The apparatus as claimed in claim 15 further comprising filtering means for filtering the modulated IR energy into wavelengths corresponding to the absorption characteristics of the liquid flowing through the venturi.

18. The apparatus as claimed in claim 15 further comprising alarm means for emitting a signal indicating that a gas bubble larger than a threshold size is present or that there is no liquid in the tube or venturi.

19. An apparatus for detecting gas bubbles in a liquid flowing through a tube comprising:

a sample area comprising a venturi formed in said sample tube through which liquid flows;

an IR energy source directed onto the liquid flowing through said sample area;

frequency modulation means for modulating the intensity of IR energy that is directed onto the sample area by said IR energy source;

an IR energy detector for sensing the IR energy incident to said detector and providing an output signal that is proportional to the amount of IR energy absorbed by the liquid flowing through said sample area; and means for processing said output signal to determine the size of any gas bubble in the liquid flowing through said sample area as a function of the amount of energy absorbed by said liquid and time.

20. The apparatus as claimed in claim 19 wherein said means for processing said output signal comprises circuitry which derives a time-varying vector magnitude signal proportional to the size of any detected gas bubble in the liquid flowing through said sample area.

21. The apparatus as claimed in claim 20 wherein said processing means further comprises amplitude demodulation means for processing said output signal for detecting gas bubbles which remain in said sample area for longer than a threshold period of time.

22. An apparatus for detecting gas bubbles in a liquid flowing through a sample tube comprising:
a sample area comprising a venturi formed in said sample tube through which liquid flows;
an IR energy source directed onto the liquid flowing through said sample area;
a frequency modulator circuit for modulating the power supply to said IR energy source at a selected duty cycle; and
an IR detector for sensing the IR energy incident to said detector and providing an output signal that is proportional to the amount of IR energy absorbed by the liquid flowing through said sample area;
wherein the selected duty cycle of said IR energy source is approximately 20% when said apparatus is detecting air bubbles and said flowing liquid is water.

23. The apparatus as claimed in claim 22 wherein said IR energy source comprises an incandescent lamp.

24. The apparatus as claimed in claim 22 further comprising means for processing said output signal to determine the size of any gas bubble in the liquid flowing through said sample area as a function of the amount of energy absorbed by said liquid and time.

25. The apparatus as claimed in claim 24 wherein said means for processing said output signal comprises circuitry which derives a time-varying vector magnitude signal proportional to the size of any detected gas bubble in the liquid flowing through said sample area.

26. The apparatus as claimed in claim 25 wherein said processing means further comprises amplitude demodulation means for processing said output signal for detecting gas bubbles which remain in said sample area for longer than a threshold period of time.

* * * * *